US011504070B2

(12) United States Patent
Jos et al.

(10) Patent No.: US 11,504,070 B2
(45) Date of Patent: Nov. 22, 2022

(54) APPARATUS AND METHOD FOR ESTIMATION CONCENTRATION OF BLOOD COMPOUND

(71) Applicant: SAMSUNG ELECTRONICS CO., LTD., Suwon-si (KR)

(72) Inventors: Sujit Jos, Bangalore (IN); Srikanth Mallavarapu Rama, Bangalore (IN); Kiran Bynam, Bangalore (IN); So Young Lee, Daejeon (KR); Gorish Aggarwal, Bangalore (IN)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 345 days.

(21) Appl. No.: 16/282,422

(22) Filed: Feb. 22, 2019

(65) Prior Publication Data
US 2019/0261928 A1    Aug. 29, 2019

(30) Foreign Application Priority Data

Feb. 23, 2018 (IN) .............................. 201841006969
Jan. 10, 2019 (KR) ........................ 10-2019-0003483

(51) Int. Cl.
*A61B 5/00* (2006.01)
*A61B 5/1455* (2006.01)
(Continued)

(52) U.S. Cl.
CPC .......... *A61B 5/7275* (2013.01); *A61B 5/1455* (2013.01); *A61B 5/14532* (2013.01);
(Continued)

(58) Field of Classification Search
CPC . A61B 5/7275; A61B 5/14532; A61B 5/1455; A61B 5/7203; A61B 5/7278; A61B 5/0075; G01N 21/274; G01N 21/359
See application file for complete search history.

(56) References Cited

U.S. PATENT DOCUMENTS

| 5,553,615 A * | 9/1996 | Carim ................ A61B 5/14535 356/39 |
| 5,991,653 A | 11/1999 | Richards-Kortum et al. |

(Continued)

FOREIGN PATENT DOCUMENTS

| EP | 1 335 199 A1 | 8/2003 |
| EP | 3 381 368 A1 | 10/2018 |

(Continued)

OTHER PUBLICATIONS

Xiaomu Song, T. Ji and A. M. Wyrwicz, "Baseline drift and physiological noise removal in high field FMRI data using kernel PCA," 2008 IEEE International Conference on Acoustics, Speech and Signal Processing, 2008, pp. 441-444, doi: 10.1109/ICASSP.2008.4517641. (hereinafter—Song) (Year: 2008).*

(Continued)

*Primary Examiner* — Devin B Henson
*Assistant Examiner* — Joseph A Tombers
(74) *Attorney, Agent, or Firm* — Sughrue Mion, PLLC

(57) ABSTRACT

A method of estimating concentration of a blood compound may include: removing a baseline drift from Near-Infrared (NIR) spectroscopy data to obtain drift-free spectral features; obtaining a set of global features based on the drift-free spectral features; and estimating the concentration of the blood compound by regression using the set of global features.

14 Claims, 9 Drawing Sheets

(51) Int. Cl.
*G01N 21/27* (2006.01)
*G01N 21/359* (2014.01)
*A61B 5/145* (2006.01)

(52) U.S. Cl.
CPC .......... *A61B 5/7203* (2013.01); *A61B 5/7278* (2013.01); *G01N 21/274* (2013.01); *G01N 21/359* (2013.01); *A61B 5/0075* (2013.01)

(56) References Cited

U.S. PATENT DOCUMENTS

| | | | |
|---|---|---|---|
| 7,438,855 | B2 | 10/2008 | Sota et al. |
| 2003/0023148 | A1* | 1/2003 | Lorenz .................. A61B 5/1495 600/300 |
| 2003/0031597 | A1 | 2/2003 | Sota et al. |
| 2004/0092804 | A1 | 5/2004 | Rebec et al. |
| 2007/0299617 | A1 | 12/2007 | Willis |
| 2008/0045820 | A1 | 2/2008 | Rebec et al. |
| 2008/0045821 | A1 | 2/2008 | Rebec et al. |
| 2011/0009720 | A1 | 1/2011 | Kunjan et al. |
| 2013/0261406 | A1 | 10/2013 | Rebec et al. |
| 2015/0164385 | A1 | 6/2015 | Varsavsky et al. |
| 2015/0177257 | A1 | 6/2015 | Albrecht et al. |
| 2016/0029966 | A1 | 2/2016 | Salas-Boni et al. |
| 2016/0073964 | A1 | 3/2016 | Cobelli et al. |
| 2016/0242687 | A1 | 8/2016 | Fujita et al. |
| 2017/0303830 | A1* | 10/2017 | Klein .................. A61B 5/6815 |
| 2018/0271448 | A1 | 9/2018 | Bynam et al. |

FOREIGN PATENT DOCUMENTS

| | | |
|---|---|---|
| EP | 3 474 288 A1 | 4/2019 |
| WO | 20180194056 A1 | 10/2018 |

OTHER PUBLICATIONS

Berthe, Dr Kya Abraham et al. "Automatic Baseline Extraction Based on PCA (Principal Component Analysis) method." 2017 (Year: 2017).*
Communication dated Apr. 18, 2019, issued by the European Patent Office in counterpart European Application No. 19158769.0.
Zhang, et al., "Non-invasive blood glucose estimation using Near-Infrared spectroscopy based on SVR", Oct. 3, 2017, IEEE 3rd Information Technology and Mechatronics Engineering Conference, XP03327169, 6 pages total (p. 594-598).
Communication dated Sep. 27, 2022, issued by the European Patent Office in counterpart European Application No. 19158769.0.
Anonymous, "Similarity measure—Wikipedia," Last edited Aug. 22, 2022, Total 3 pages, XP055963389, Retrieved from: https://en.wikipedia.org/wiki/Similarity_measure.

* cited by examiner

APPARATUS AND METHOD FOR ESTIMATION CONCENTRATION OF BLOOD COMPOUND

CROSS-REFERENCE TO RELATED APPLICATION(S)

This application claims priority from Indian Patent Application No. 201841006969, filed on Feb. 23, 2018 in the Indian Patent Office, and Korean Patent Application No. 10-2019-0003483, filed on Jan. 10, 2019 in the Korean Intellectual Property Office, the disclosures of which are incorporated herein by reference in their entireties.

BACKGROUND

1. Field

Apparatuses and methods consistent with exemplary embodiments relate to estimating concentration of a blood compound using Near-Infrared (NIR) spectroscopy data in a non-invasive manner.

2. Description of the Related Art

Monitoring of concentration of blood compounds has always been a topic of much interest. The monitoring of concentration of the blood compounds are typically performed invasively wherein the skin of a test (human or animal) subject is pierced to obtain a blood sample for testing. In a non-invasive method, collection of blood sample is not required for prediction of concentration of the blood compound. Also, the non-invasive method provides a painless means of blood compound monitoring especially for those who need to check the concentration of a particular compound several times a day. Some of the typical methods used for monitoring the concentration of blood compounds non-invasively are Mid-Infrared (Mid-IR), Near-Infrared (NIR), and Raman spectroscopy.

Of the above methods, the NIR spectroscopy is widely used for monitoring concentration of blood compounds. However, the prediction of a particular compound concentration based on NIR spectroscopy data is very challenging when the particular compound's concentration is to be calculated in the presence of other compounds that are not of interest. For example, when monitoring the glucose concentration in the blood, the other compounds in the blood such as water, collagen, keratin, cholesterol, etc. acts as interfering compounds. Another major challenge is to remove drift component from the NIR spectroscopy data that adversely affects the features used for prediction. This in turn affects the prediction accuracy of the blood compound based on the NIR spectroscopy data.

In a related method, drift noise is removed by using an optimal filter. However, the method requires an error covariance matrix which is not possible to compute accurately. In another related method, a baseline scatter removal algorithm is used to compute drifts associated with multiple spectra simultaneously. However, the method requires continuous measurements with the same compound concentration, and therefore it is not suitable for blood composition analysis.

Therefore, there is a need for a method of removing drift from the NIR spectroscopic data for monitoring of concentration of compounds in the blood. Furthermore, there is also a need to obtain a set of global features that could be used for prediction of the concentration of the blood compound using regression.

SUMMARY

Example embodiments address at least the above problems and/or disadvantages and other disadvantages not described above. Also, the example embodiments are not required to overcome the disadvantages described above, and may not overcome any of the problems described above.

According to an aspect of an example embodiment, there is provided a method of estimating concentration of a blood compound, the method including: removing a baseline drift from Near-Infrared (NIR) spectroscopy data to obtain drift-free spectral features; obtaining a set of global features based on the drift-free spectral features; and estimating the concentration of the blood compound by regression using the set of global features.

The removing the baseline drift from the NIR spectroscopy data may include removing the baseline drift from the NIR spectroscopy data using principal component analysis (PCA).

The removing baseline drift from the NIR spectroscopy data may include: computing a plurality of principal components of the NIR spectroscopy data; obtaining a drift approximation from the plurality of principal components; obtaining a spectral drift approximation from the drift approximation for each spectral feature according to a magnitude of the spectral feature; and removing respective spectral drift approximation from each spectral feature to obtain the drift-free spectral features.

The obtaining the drift approximation from the plurality of principal components may include: selecting a principal component that characterizes the baseline drift, from among the plurality of principal components, based on a change in the principal component over time; and obtaining a polynomial approximation of a predefined degree of the selected principal component as the drift approximation.

The selecting the principal component that characterizes the baseline drift may include selecting a first principal component from among the plurality of principal components as the principal component that characterizes the baseline drift.

The obtaining the polynomial approximation of the predefined degree of the selected principal component as the drift approximation may include obtaining, as the drift approximation, the polynomial approximation that minimizes a least squared error between the polynomial approximation and the baseline drift.

The obtaining the spectral drift approximation from the drift approximation may include: normalizing the drift approximation; and obtaining the spectral drift approximation by scaling the normalized drift approximation by an amplitude-span of the spectral feature.

The normalizing the drift approximation may include dividing the drift approximation by an amplitude-span of the drift approximation to obtain the normalized drift approximation.

The obtaining the set of global features comprises: obtaining similarity values of each drift-free spectral feature with a compound vector; obtaining a similarity metric for each drift-free spectral feature using the similarity values; ranking the drift-free spectral features based on the similarity metric; and selecting a predefined number of drift-free spectral features as the set of global features.

According to an aspect of another example embodiment, there is provided a blood compound concentration prediction apparatus including at least one processor including: a drift removal unit configured to remove a baseline drift from Near-Infrared (NIR) spectroscopy data to obtain drift-free spectral features; a global feature extraction unit configured to obtain a set of global features based on the drift-free spectral features; and a prediction unit configured to estimate a concentration of a blood compound by regression using the set of global features.

The drift removal unit may remove the baseline drift from the NIR spectroscopy data using principal component analysis (PCA).

The drift removal unit: may compute a plurality of principal components of the NIR spectroscopy data; may obtain a drift approximation from the plurality of principal components; may obtain a spectral drift approximation from the drift approximation for each spectral feature according to a magnitude of the spectral feature; and may remove respective spectral drift approximation from each spectral feature to obtain the drift-free spectral features.

The drift removal unit: may select a principal component that characterizes the baseline drift, from among the plurality of principal components, based on a change in the principal component over time; and may obtain a polynomial approximation of a predefined degree of the selected principal component as the drift approximation.

The drift removal unit may select a first principal component from among the plurality of principal components as the principal component that characterizes the baseline drift.

The drift removal unit may obtain as the drift approximation, a polynomial approximation that minimizes a least squared error between the polynomial approximation and the baseline drift.

The drift removal unit: may normalize the drift approximation; and may obtain the spectral drift approximation by scaling the normalized drift approximation by an amplitude-span of the spectral feature.

The drift removal unit may divide the drift approximation by an amplitude-span of the drift approximation to obtain the normalized drift approximation.

The global feature extraction unit: may obtain similarity values of each drift-free spectral feature with a compound vector; may obtain a similarity metric for each drift-free spectral feature using the obtained similarity values; may rank the drift-free spectral features as per the similarity metric; and may select a predefined number of drift-free spectral features as the set of global features.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1A:
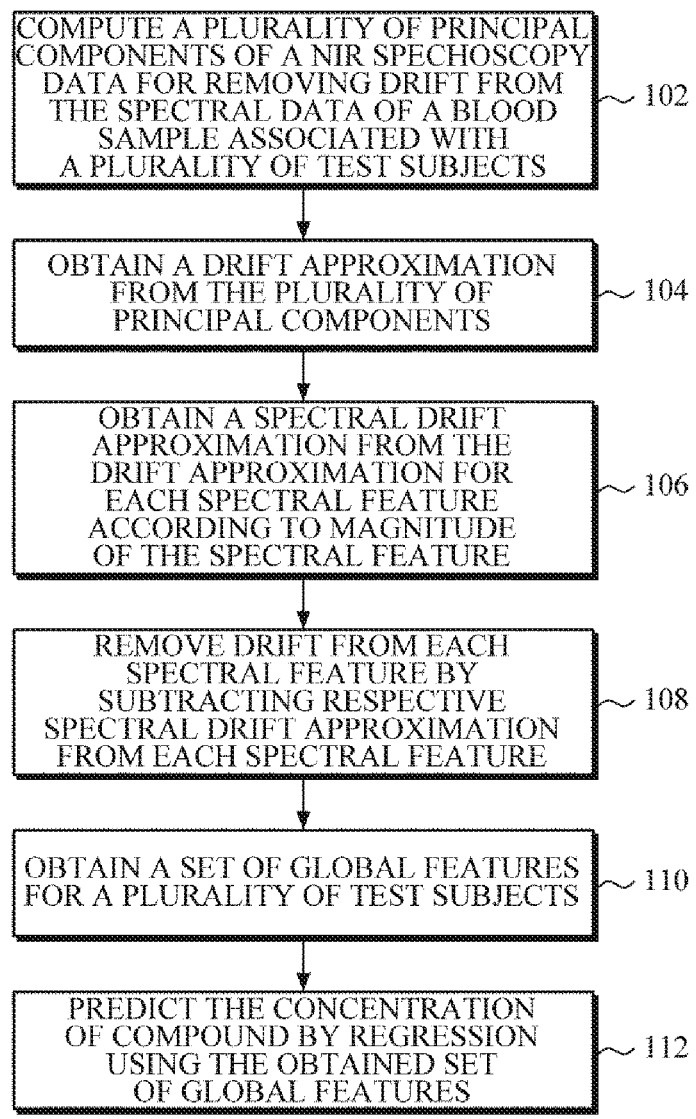
FIG. 1A is a flowchart diagram illustrating a method of predicting concentration of a blood compound of interest non-invasively using Near-Infrared spectroscopy data, according to one example embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

The specification may refer to "an", "one" or "some" embodiment(s) in several locations. This does not necessarily imply that each such reference is to the same embodiment(s), or that the feature only applies to a single embodiment. Single features of different embodiments may also be combined to provide other embodiments.

As used herein, the singular forms "a", "an" and "the" are intended to include the plural forms as well, unless expressly stated otherwise. It will be further understood that the terms "includes", "comprises", "including" and/or "comprising" when used in this specification, specify the presence of stated features, integers, steps, operations, elements and/or components, but do not preclude the presence or addition of one or more other features, integers, steps, operations, elements, components, and/or groups thereof. As used herein, the term "and/or" includes any and all combinations and arrangements of one or more of the associated listed items.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Unless otherwise defined, all terms (including technical and scientific terms) used herein have the same meaning as commonly understood by one of ordinary skill in the art to which this disclosure pertains. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The embodiments herein and the various features and advantages details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein can be practiced and to further enable those of skill in the art to practice the embodiments herein. Accordingly, the examples should not be construed as limiting the scope of the embodiments herein.

An example embodiment provides a method for predicting concentration of a blood compound non-invasively using NIR spectroscopy. The embodiment provides a drift removal algorithm which makes use of information from principal components of the NIR spectroscopy data for the drift removal process. The term "drift" may refer to a baseline drift of a bio-signal, such as a photoplethysmogram (PPG) signal, an electromyography (EMG) signal, or an electrocardiography (ECG) signal. The embodiment further provides extraction of a set of global features for prediction of the concentration of the blood compound using regression. The same is illustrated in FIG. 1A. FIG. 1A is a flowchart diagram illustrating a method of predicting concentration of a blood compound of interest non-invasively using Near-Infrared spectroscopy data, according to one example embodiment. The step by step process for predicting the concentration of the blood compound of interest using the present prediction method is explained herein as follows. In operation 102, a plurality of principal components of a NIR spectroscopy data set are computed according to principal component analysis (PCA). In operation 104, a drift approximation from the plurality of principal components is obtained. For example, the drift approximation have a value that minimizes a least-squared error $\|p'_c - p_c\|^2$, wherein $p'_c$ denotes the drift approximation and $p_c$ denotes a principal component (e.g., a first principal component) selected from the plurality of principal components. In another example, the drift approximation is a polynomial approximation that is obtained based on Remez algorithm. Further, a spectral drift approximation from the drift approximation for each spectral feature according to magnitude of the spectral feature is obtained in operation 106. Then, drift from the spectral features is removed by subtracting respective spectral drift approximation from each spectral feature in operation 108. Upon removing the drift from the spectral features, a set of global features for a plurality of test subjects are obtained in operation 110. Finally, the concentration of the compound is estimated by regression using the obtained set of global features in operation 112.

Figure 1B:
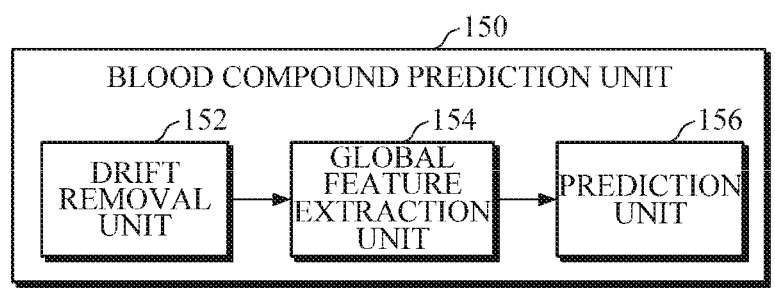
FIG. 1B is a block diagram illustrating a blood compound concentration prediction apparatus, according to one example embodiment.

FIG. 1B is a block diagram illustrating a blood compound concentration prediction apparatus, according to one example embodiment. The blood compound concentration prediction apparatus 150 may be embedded in an electronic apparatus. Examples of the electronic apparatus may include a cellular phone, a smartphone, a tablet PC, a laptop computer, a personal digital assistant (PDA), a portable multimedia player (PMP), a navigation device, an MP3 player, a digital camera, a wearable device, and the like, and examples of the wearable device may include a watch-type device, a wristband-type device, a ring-type device, a waist belt-type device, a necklace-type device, an ankle band-type device, a thigh band-type device, a forearm band-type device, and the like. However, the electronic device is not limited to the above examples, and the wearable device is neither limited thereto.

According to one example embodiment, the blood compound concentration prediction apparatus 150 may include a drift removal unit 152, global feature extraction unit 154 and a prediction unit 156. The drift removal unit 152, the global feature extraction unit 154 and the prediction unit 156 may be implemented by one or more processors. The drift removal unit 152 computes and removes drift from the NIR spectroscopy data. In detail, the NIR spectroscopy data is obtained as follows.

At first, the value of a blood compound is obtained using a standard invasive procedure (e.g., a blood pressure measurement using a cuff). Then, a non-invasive spectral scan is performed on a person/test subject using near-Infrared spectrometer to obtain raw NIR spectra. The raw NIR spectra is labelled as a blood compound value which was obtained from the invasive procedure, and is stored in the blood compound concentration prediction apparatus 150. The obtained raw NIR spectra are preprocessed further to obtain compound spectra. The compound spectra and the associated compound values may be arranged into the form of the matrix X using data obtained in consecutive measurements, which would be referred as data matrix in the rest of the document.

$$X = \begin{bmatrix} c^1 & s^1_{\lambda_0} & s^1_{\lambda_1} & \cdots & s^1_{\lambda_{n-1}} \\ c^2 & s^2_{\lambda_0} & s^2_{\lambda_1} & \cdots & s^2_{\lambda_{n-1}} \\ & & \cdots & & \\ c^N & s^N_{\lambda_0} & s^N_{\lambda_1} & \cdots & s^N_{\lambda_{n-1}} \end{bmatrix} = [c \,|\, S]$$

Here, $c = [c^1 \, c^2 \ldots c^N]^T$ is a compound vector. The matrix S is the NIR spectroscopy data. The NIR spectroscopy data is affected by the drift which in turn affects the prediction accuracy of the compound of interest. Each column of the matrix S is the absorption spectra associated with the wavelength $\lambda$ and may be represented by the vector $s_\lambda$. It may be noted that the absorption spectra $s_\lambda$ in some embodiments can be interchangeably referred to as "spectral feature" or "feature".

$$s_\lambda = [s_\lambda^1 \, s_\lambda^2 \, s \ldots s_\lambda^N]$$

The absorption spectra $s_\lambda$ could be written as $$s_\lambda = s_\lambda^t + f_\lambda$$

Here, $s_\lambda^t$ is the true absorption spectra and $f_\lambda$ is the drift affecting the true absorption spectra.

The drift removal unit 152 obtains an estimate of the drift component $f'_\lambda$ and subtracts it from $s_\lambda$ to obtain the drift-free spectra $\widetilde{s}_\lambda(t)$ which is expressed as:

$$\widetilde{s}_\lambda = s_\lambda - f'_\lambda$$

In one example embodiment, the drift removal unit 152 removes drift using principal component analysis (PCA). The drift removal unit 152 performs the PCA operation for obtaining the $i^{th}$ principal component $P_c^i$ which is described as $$Z = PCA(S)$$

$$p_c^i = S * Z(:, i)$$

Here, the variables follow the standard notations. If the drift component on the data set is significant enough to impact the predictions based on the set, it is likely to manifest in the first principal component of the data set. Else, the drift would manifest in say $i^{th}$ principal component. Also, since all the principal components are uncorrelated, it is a reasonable assumption that if the drift component is captured in the $i^{th}$ principal component, it is unlikely that it would significantly manifest in any other principal components. Let the $i^{th}$ Principal component in which drift is manifested be denoted by $p_c$. In an example embodiment, the first principal component may be selected from a plurality of principal components to remove the drift component when the change in the value of the first principal component over time is greater than a predetermined value.

Figure 2A:
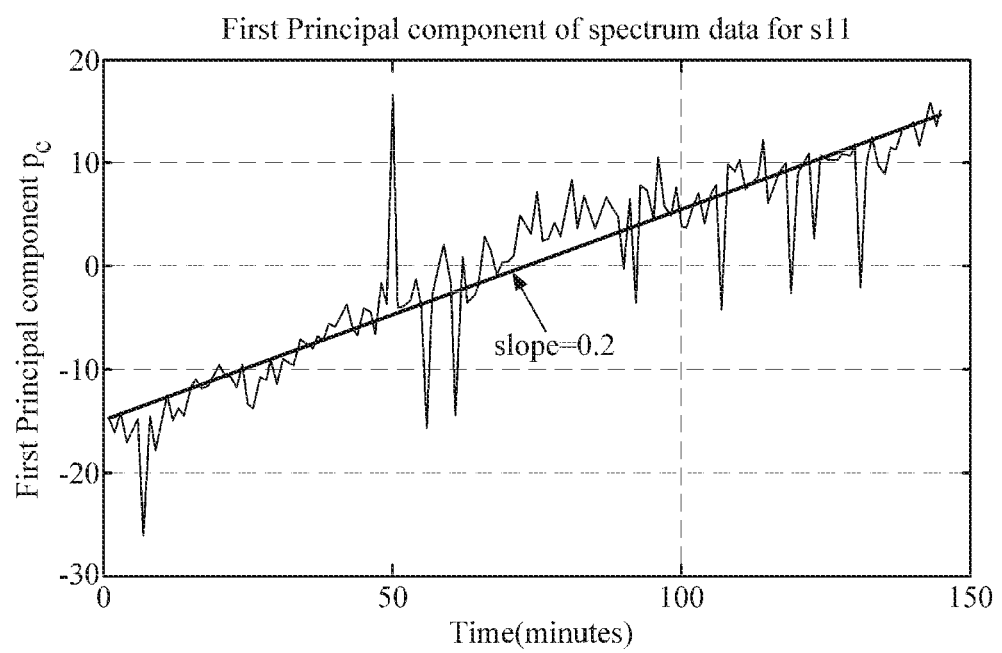
FIG. 2A illustrates a graphical representation of a first principal component and corresponding linear approximation of the NIR spectroscopy data of a test subject S11, according to one example embodiment.
Figure 2B:
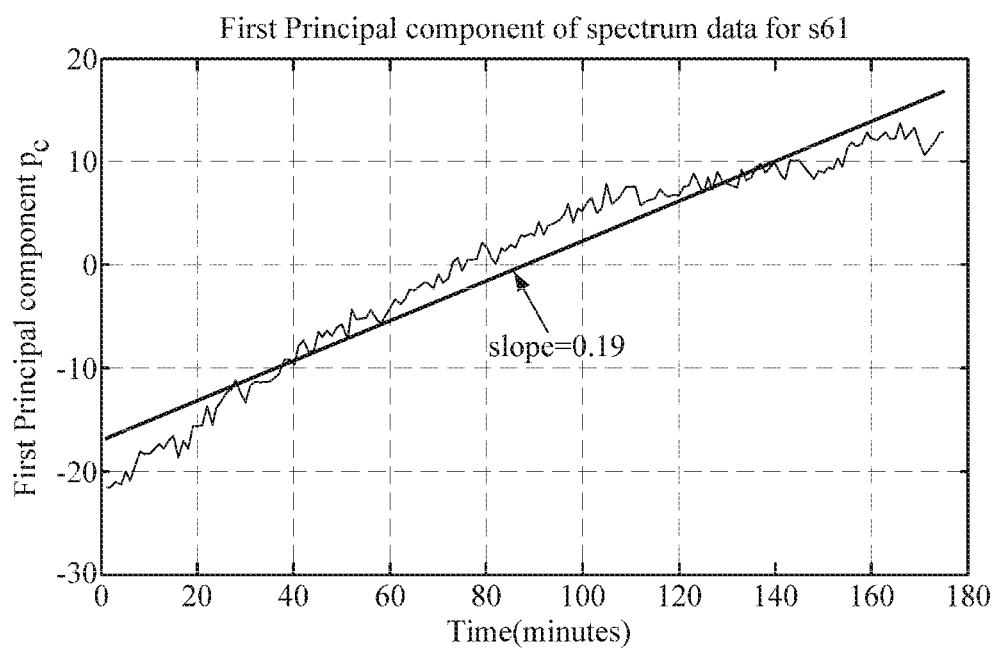
FIG. 2B illustrates a graphical representation of a first principal component and corresponding linear approximation of the NIR spectroscopy data of a test subject S61, according to one example embodiment.
Figure 2C:
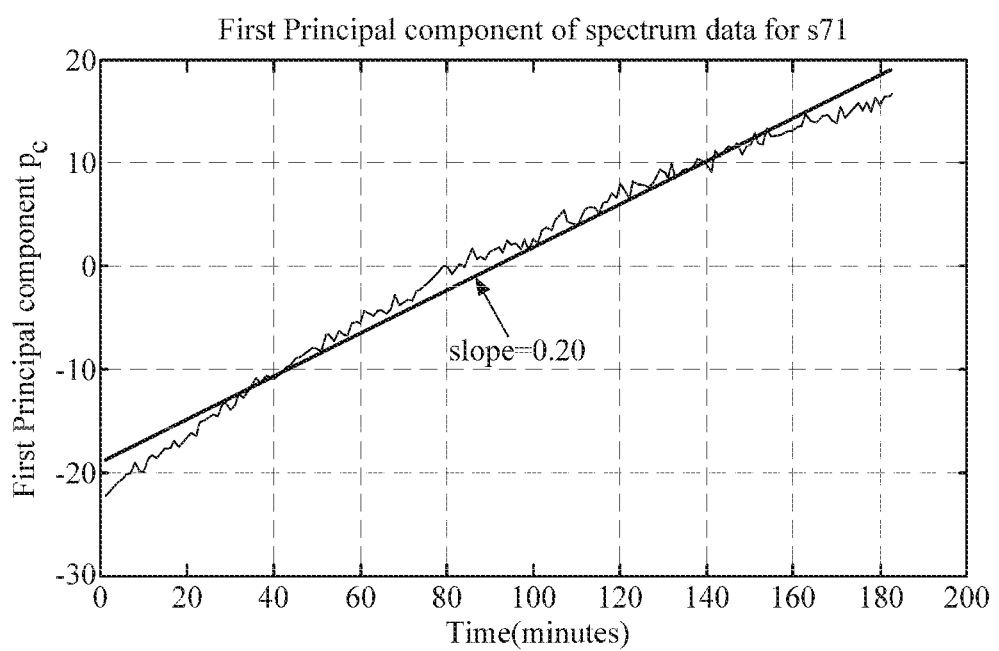
FIG. 2C illustrates a graphical representation of a first principal component and corresponding linear approxima-tion of the NIR spectroscopy data of a test subject S71, according to one example embodiment.

FIGS. 2A to 2C illustrate a graphical representation of a first principal component and corresponding linear approximation of NIR spectroscopy data of different test subjects labelled S11, S61, and S71 according to one example embodiment. As shown in FIGS. 2A to 2C, there is a predominance of the drift component. The slope of the linear approximation gives the rate of change of the drift with respect to the time.

Figure 3:
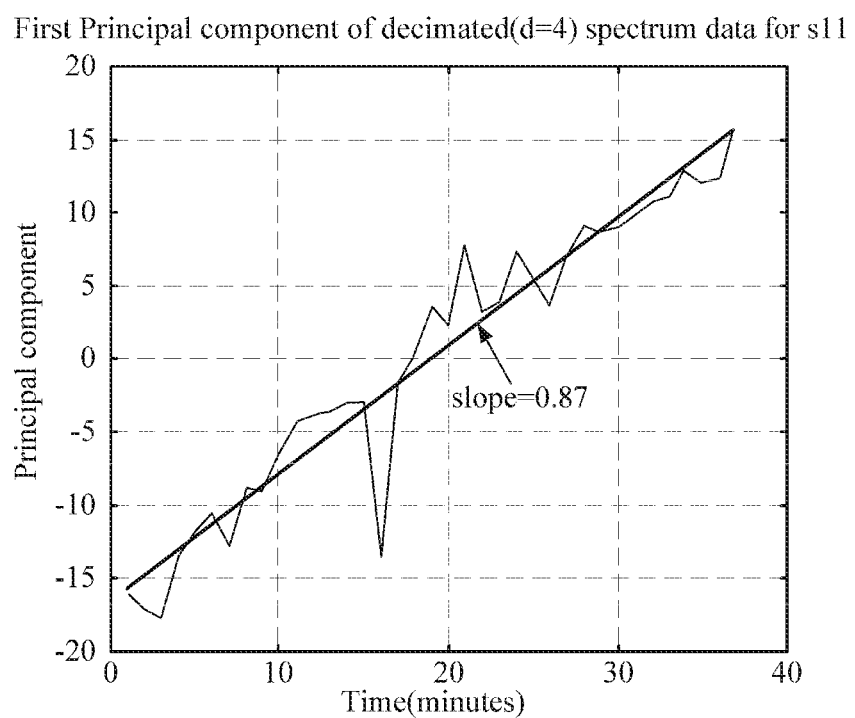
FIG. 3 illustrates a first principal component of a 4-decimation of NIR spectroscopy data corresponding to test subject S11, according to one example embodiment.

FIG. 3 illustrates the first principal component of 4-decimation of the NIR spectroscopy data of test subject S11, according to one example embodiment. The NIR spectroscopy data is expressed as:

$$S = \begin{bmatrix} s^1_{\lambda_0} & s^1_{\lambda_1} & \cdots & s^1_{\lambda_{n-1}} \\ s^2_{\lambda_0} & s^2_{\lambda_1} & \cdots & s^2_{\lambda_{n-1}} \\ & & \cdots & \\ s^N_{\lambda_0} & s^N_{\lambda_1} & \cdots & s^N_{\lambda_{n-1}} \end{bmatrix} = \begin{bmatrix} x^0 \\ x^1 \\ \cdots \\ x^{N-1} \end{bmatrix}$$

The d-decimation of S is defined as $$S^d = \begin{bmatrix} x^0 \\ x^d \\ x^{2d} \\ x^{3d} \\ \vdots \\ \vdots \end{bmatrix}$$

The set $S^d$ is obtained by including every $d^{th}$ row of the matrix S. As shown in FIG. 3, the first principal component of $S^d$ is characterized by a linear approximation whose slope is approximately 4 times the slope of the original matrix S in FIG. 2A. This demonstrates that the drift component is captured in the first principal component in this example.

Figure 4:
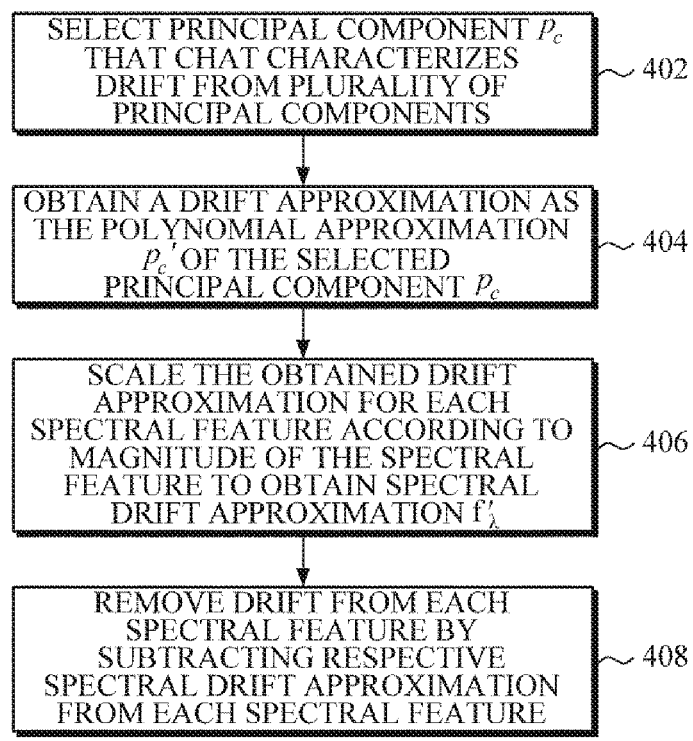
FIG. 4 is a flowchart diagram illustrating a method of removing drift using principal component analysis, according to one example embodiment.

FIG. 4 is a flowchart diagram illustrating a method of removing drift using principal component analysis, according to one example embodiment. According to this example embodiment, the drift removal unit 152 removes drift using principal component analysis. The step by step process performed by the drift removal unit 152 is explained herein as follows. In operation 402, a principal component $p_c$ that characterizes drift is selected from a plurality of principal components. In operation 404, the polynomial approximation $p_c'$ of the selected principal component $p_c$ is obtained as a drift approximation. In one example embodiment, drift approximation $p_c'$ may be obtained as $p_c'$ that minimizes the least squared error $\|p_c' - p_c\|^2$. Further, in operation 406, for each $s_\lambda$, the drift approximation is scaled as per the magnitude of $s_\lambda$ to obtain spectral drift approximation $f'_\lambda$. The spectral drift approximation $f'_\lambda$ is obtained as $$f'_\lambda = \frac{d_s}{d_p} * p'_c$$

Here, $d_s$ is the amplitude span of $s_\lambda$ given by $d_s = (\max(s_\lambda) - \min(s_\lambda))$ and $d_p$ is the amplitude span of $P'_c$ given by $d_p = (\max(p'_c) - \min(p'_c))$.

Finally, in operation 408, the drift removal is performed by subtracting the spectral drift approximation $f'_\lambda$ from the respective $s_\lambda$ for every $\lambda$. This is represented as $$\widetilde{s_\lambda} = s_\lambda - f'_\lambda, \lambda = \lambda_0, \lambda_1, \ldots \lambda_{n-1}$$

The $\widetilde{s_\lambda}$ is also referred to as drift-free spectral feature or simply drift-free feature.

Figure 5:
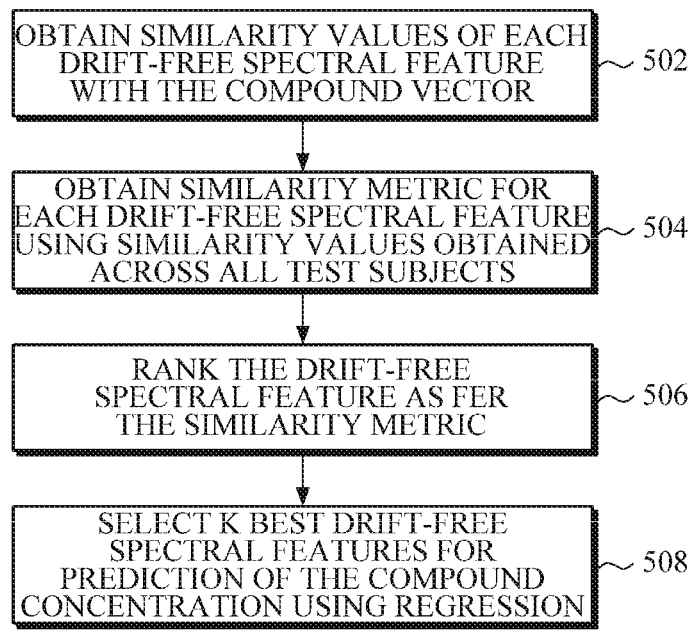
FIG. 5 is a flowchart diagram illustrating one or more steps involved in global feature extraction for compound's concentration prediction, according to one example embodiment.

FIG. 5 is a flowchart diagram illustrating a method of extracting global features for prediction of concentration of compound, according to one example embodiment. In this example embodiment, one or more operations performed by a global feature extraction unit 154 for extracting global features are explained herein as follows. In operation 502, a similarity value of each drift-free spectral feature with the respective compound vector is obtained. Let there be P test subjects denoted as $S_k^{test}$, k=1, 2, ..., P. Let the corresponding drift-free spectral features for the subject $S_k^{test}$ be denoted as $\widetilde{s_\lambda^k}$ and the compound's concentration be denoted by $c^k$. In one example embodiment, the similarity value may be obtained as the correlation of the drift-free spectral feature $\widetilde{s_\lambda^k}$ with the compound vector $c^k$, which may be computed as $$\Psi_k(\lambda) = \langle c^k, \widetilde{s_\lambda^k} \rangle$$

In operation 504, similarity metric for each drift-free spectral feature is obtained using similarity values obtained across all test subjects. In one example embodiment, the similarity metric may be computed as $$R(\lambda) = \Sigma_k \Psi_k^2(\lambda)$$

In operation 506, the drift-free spectral features are ranked as per the similarity metric. In operation 508, a K number of drift-free spectral features are selected in order of the ranking for prediction of the compound concentration using regression. The number K may have a predetermined value, and/or may be decided based on the performance of particular regression method employed for prediction. The K number of drift-free features are referred to as "global features" in rest of the document.

Now, based on the obtained global features, the prediction unit 156 predicts or estimates concentration of the blood compound using regression from the drift free spectroscopy data.

Figure 6:
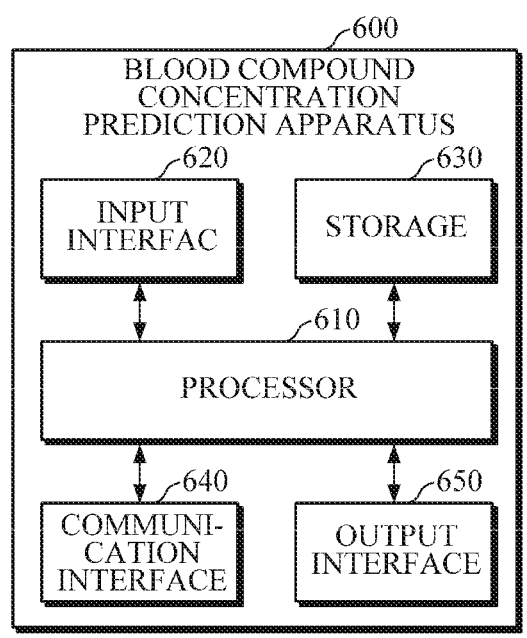
FIG. 6 is a block diagram illustrating a blood compound concentration prediction apparatus, according to another example embodiment.

FIG. 6 is a block diagram illustrating a blood compound concentration prediction apparatus, according to another example embodiment. The blood compound concentration prediction apparatus 600 may be embedded in an electronic apparatus. Examples of the electronic apparatus may include a cellular phone, a smartphone, a tablet PC, a laptop computer, a personal digital assistant (PDA), a portable multimedia player (PMP), a navigation device, an MP3 player, a digital camera, a wearable device, and the like, and examples of the wearable device may include a watch-type device, a wristband-type device, a ring-type device, a waist belt-type device, a necklace-type device, an ankle band-type device, a thigh band-type device, a forearm band-type device, and the like. However, the electronic device is not limited to the above examples, and the wearable device is neither limited thereto.

Referring to FIG. 6, the blood compound concentration prediction apparatus 600 includes a processor 610, an input interface 620, a storage 630, a communication interface 640, and an output interface 650. Here, the processor 610 may perform the operations of the drift removal unit 152, the global feature extraction unit 154, and the prediction unit 156 described above with reference to FIGS. 1 to 5, such that detailed description thereof will be omitted.

The input interface 620 may receive NIR spectroscopy data, and may receive input of various operation signals from a user. In the embodiment, the input interface 620 may include a keypad, a dome switch, a touch pad (static pressure/capacitance), a jog wheel, a jog switch, a hardware (H/W) button, and the like. Particularly, the touch pad, which forms a layer structure with a display, may be called a touch screen.

The storage 630 may store programs or commands for operation of the blood compound concentration prediction apparatus 600, and may store data input to and output from the blood compound concentration prediction apparatus 600 and data processed by the blood compound concentration prediction apparatus 600, and the like.

The storage 630 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the blood compound concentration prediction apparatus 600 may operate an external storage medium, such as web storage and the like, which performs a storage function of the storage 630 on the Internet.

The communication interface 640 may communicate with an external device. For example, the communication interface 640 may transmit, to the external device, the data input to the blood compound concentration prediction apparatus 600, data stored in and processed by the blood compound concentration prediction apparatus 600, and the like, or may receive, from the external device, various data useful for estimating a blood compound concentration.

In this case, the external device may be medical equipment using the data input to the blood compound concentration prediction apparatus 600, data stored in and processed by the blood compound concentration prediction apparatus 600, and the like, a printer to print out results, or a display device. In addition, the external device may be a digital TV, a desktop computer, a cellular phone, a smartphone, a tablet PC, a laptop computer, a personal digital assistant (PDA), a portable multimedia player (PMP), a navigation device, an MP3 player, a digital camera, a wearable device, and the like, but is not limited thereto.

The communication interface 640 may communicate with external devices by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra Wideband (UWB) communication, Ant+ communication, WIFI communication, Radio Frequency Identification (RFID) communication, 3G communication, 4G communication, 5G communication, and the like. However, this is merely exemplary and communication is not limited thereto.

The output interface 650 may output the data input to the blood compound concentration prediction apparatus 600, data stored in and processed by the blood compound concentration prediction apparatus 600, and the like. In the embodiment, the output interface 650 may output the data input to the blood compound concentration prediction apparatus 600, data stored in and processed by the blood compound concentration prediction apparatus 600, and the like, by using at least one of an acoustic method, a visual method, and a tactile method. To this end, the output interface 650 may include a display, a speaker, a vibrator, and the like.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A method of estimating concentration of a blood compound, the method comprising
    removing a baseline drift from Near-Infrared (NIR) spectroscopy data to obtain drift-free spectral features, wherein the removing the baseline drift comprises:
        obtaining a linear drift approximation of the NIR spectroscopy data;
        scaling the linear drift approximation of the NIR spectroscopy data by a ratio between an amplitude span of a plurality of spectral features of the NIR spectroscopy data and an amplitude span of a plurality of principal components of the NIR spectroscopy data;
        subtracting the scaled linear drift approximation from the NIR spectroscopy data to obtain the drift-free spectral features;
    obtaining a set of global features based on the drift-free spectral features; and
    estimating a concentration of the blood compound by regression using the set of global features,
    wherein the amplitude span of the plurality of spectral features is a difference between a maximum value and a minimum value of the plurality of spectral features for each wavelength, and the amplitude span of the plurality of principal components is a difference between a maximum value and a minimum value of the plurality of principal components for each wavelength.

2. The method of claim 1, wherein the removing the baseline drift from the NIR spectroscopy data comprises removing the baseline drift from the NIR spectroscopy data using principal component analysis (PCA).

3. The method of claim 1, wherein the obtaining the set of global features comprises:

obtaining similarity values between each of the drift-free spectral features and a compound vector consisting of a set of reference values;

ranking the drift-free spectral features based on the similarity values between each of the drift-free spectral features and the compound vector consisting of the set of reference values; and based on rankings of the drift-free spectral features, selecting a predefined number of drift-free spectral features as the set of global features.

4. The method of claim 1, wherein the removing the baseline drift further comprises:

selecting a principal component that characterizes the baseline drift, from among the plurality of principal components, based on a change in the principal component over time; and obtaining, as the linear drift approximation, a polynomial approximation of a predefined degree of the selected principal component.

5. The method of claim 4, wherein the selecting the principal component that characterizes the baseline drift comprises selecting a first principal component from among the plurality of principal components as the principal component that characterizes the baseline drift.

6. The method of claim 4, wherein the obtaining the polynomial approximation of the predefined degree of the selected principal component comprises obtaining the polynomial approximation that minimizes a least squared error between the polynomial approximation and the baseline drift.

7. The method of claim 1, wherein the scaling the linear drift approximation comprises dividing the linear drift approximation by the ratio between the amplitude span of the plurality of spectral features of the NIR spectroscopy data and the amplitude span of the plurality of principal components of the NIR spectroscopy data.

8. A blood compound concentration prediction apparatus, comprising at least one processor configured to:

remove a baseline drift from Near-Infrared (NIR) spectroscopy data to obtain drift-free spectral features by:

obtaining a linear drift approximation of the NIR spectroscopy data;

scaling the linear drift approximation of the NIR spectroscopy data by a ratio between an amplitude span of a plurality of spectral features of the NIR spectroscopy data and an amplitude span of a plurality of principal components of the NIR spectroscopy data;

subtracting the scaled linear drift approximation from the NIR spectroscopy data to obtain the drift-free spectral features;

obtain a set of global features based on the drift-free spectral features; and estimate a concentration of a blood compound by regression using the set of global features, wherein the amplitude span of the plurality of spectral features is a difference between a maximum value and a minimum value of the plurality of spectral features for each wavelength, and the amplitude span of the plurality of principal components is a difference between a maximum value and a minimum value of the plurality of principal components for each wavelength.

9. The blood compound concentration prediction apparatus of claim 8, wherein the at least one processor is further configured to remove the baseline drift from the NIR spectroscopy data using principal component analysis (PCA).

10. The blood compound concentration prediction apparatus of claim 8, wherein the at least one processor is further configured to:

obtain similarity values between each of the drift-free spectral features and a compound vector consisting of a set of reference values;

rank the drift-free spectral features based on the similarity values between each of the drift-free spectral features and the compound vector consisting of the set of reference values; and based on rankings of the drift-free spectral features, selecting a predefined number of drift-free spectral features as the set of global features.

11. The blood compound concentration prediction apparatus of claim 8, wherein the at least one processor is further configured to:

select a principal component that characterizes the baseline drift, from among the plurality of principal components, based on a change in the principal component over time; and obtain, as the linear drift approximation, a polynomial approximation of a predefined degree of the selected principal component.

12. The blood compound concentration prediction apparatus of claim 11, wherein the at least one processor is further configured to select a first principal component from among the plurality of principal components as the principal component that characterizes the baseline drift.

13. The blood compound concentration prediction apparatus of claim 11, wherein the at least one processor is further configured to obtain the polynomial approximation that minimizes a least squared error between the polynomial approximation and the baseline drift.

14. The blood compound concentration prediction apparatus of claim 8, wherein the at least one processor is further configured to obtain the linear drift approximation by dividing the linear drift approximation by the ratio between the amplitude span of the plurality of spectral features of the NIR spectroscopy data and the amplitude span of the plurality of principal components of the NIR spectroscopy data.

* * * * *